(12) United States Patent
Ci

(10) Patent No.: US 10,918,560 B2
(45) Date of Patent: Feb. 16, 2021

(54) HEALTH MULTIFUNCTIONAL CHAIR AND CONTROL METHOD THEREFOR

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 400 days.

(21) Appl. No.: 15/954,349

(22) Filed: Apr. 16, 2018

(65) Prior Publication Data

US 2019/0314239 A1  Oct. 17, 2019

(51) Int. Cl.
*A61M 21/02* (2006.01)
*A61H 7/00* (2006.01)
*A63B 21/00* (2006.01)
*A61M 21/00* (2006.01)

(52) U.S. Cl.
CPC .............. *A61H 7/00* (2013.01); *A61M 21/02* (2013.01); *A63B 21/00178* (2013.01); *A63B 21/4034* (2015.10); *A61H 2201/10* (2013.01); *A61H 2201/5012* (2013.01); *A61H 2201/5046* (2013.01); *A61H 2201/5048* (2013.01); *A61H 2203/0431* (2013.01); *A61H 2205/081* (2013.01); *A61H 2230/045* (2013.01); *A61H 2230/201* (2013.01); *A61H 2230/305* (2013.01); *A61H 2230/505* (2013.01); *A61H 2230/625* (2013.01); *A61H 2230/855* (2013.01); *A61M 2021/0027* (2013.01); *A63B 2225/09* (2013.01)

(58) Field of Classification Search
CPC ........ A61H 2201/0149; A61H 2201/10; A61H 2201/1623; A61H 2201/1633; A61H 2201/1635; A61H 2201/501; A61H 2201/5012; A61H 2201/5048; A61H 2203/0431; A61H 2205/081; A61H 7/00; A61H 7/007; A61H 21/00178; A61M 2021/0022; A61M 2021/0027; A61M 21/02; A61M 2205/3553
See application file for complete search history.

(56) References Cited

U.S. PATENT DOCUMENTS

2009/0306555 A1\* 12/2009 Goto ........................ A61H 5/00
601/15

\* cited by examiner

*Primary Examiner* — Christine H Matthews
(74) *Attorney, Agent, or Firm* — Cantor Colburn LLP

(57) ABSTRACT

The present disclosure discloses a health multifunctional chair and a control method thereof. The multifunctional chair includes: a chair seat, a massage backrest, an exercise standing plate, and a general management system, the general management system includes: a detecting and controlling unit and a health analyzing unit; the health analyzing unit is provided locally or on a cloud, and is in communication connection with the detecting and controlling unit; the exercise standing plate is adjusted in angle with one side edge as a reference and towards a direction of the chair seat; the massage backrest is provided with a meridian massage mechanism therein; the health analyzing unit is used to acquire a health analysis result of the user, and provide a health solution. The present disclosure performs combined and ordered meridian massage to the back of the user, thus improving the quality of health maintenance.

19 Claims, 3 Drawing Sheets

HEALTH MULTIFUNCTIONAL CHAIR AND CONTROL METHOD THEREFOR

TECHNICAL FIELD

The present disclosure relates to the field of massage and health management equipment, and particularly to a health multifunctional chair and a control method thereof.

BACKGROUND

In recent years, with the concentration of urban population and the accelerated pace of life, the population in sub-health status is increased significantly. Meanwhile, with the improvement of consumption power and consumption concept of the country, people pay more attention to maintenance of their own health, thus many types of household fitness equipment are derived.

The functional chair is one of the above equipment. A main function of the functional chairs currently in the market is doing local massage to the human body, so that a user releases the life stress of the day, and further relieves functions of the body in various aspects. However, the function of the functional chairs currently in the market is unitary, and cannot satisfy requirements of high-quality and all-around maintenance of modern people.

We have now entered the age of big data of health management, and the health management with the characteristics of the traditional Chinese medicine has exerted invisible influences on people's life. Therefore, to develop a health management multifunctional chair for preserving health through the traditional Chinese medicine meridian and exercise has become a general trend of market effect.

SUMMARY

An object of the present disclosure is to provide a health multifunctional chair capable of performing finger-plucking massage and health management and a control method thereof to overcome problems existing in the prior art.

In order to achieve the above object, the present disclosure provides a health multifunctional chair. The health multifunctional chair includes: a chair seat, a massage backrest, an exercise standing plate, and a general management system, wherein the general management system includes: a detecting and controlling unit and a health analyzing unit; the health analyzing unit is provided locally or on a cloud, and is in communication connection with the detecting and controlling unit; the massage backrest is reversibly provided at one side of the chair seat, and the exercise standing plate is provided at the other side of the chair seat; the exercise standing plate can be adjusted in angle with one side edge as a reference and towards a direction of the chair seat; the massage backrest is provided with a meridian massage mechanism therein, and the meridian massage mechanism is used to do massage to a back; the health analyzing unit is used to analyze health information of a user collected by the detecting and controlling unit, acquire a health analysis result of the user, and provide a health solution; the detecting and controlling unit is further used to control massage of the meridian massage mechanism to corresponding human body positions and angle adjustment of the exercise standing plate.

Furthermore, with respect to the health multifunctional chair as described above, the massage backrest is further provided with a 3D positioning module therein, the 3D positioning module is electrically connected to the detecting and controlling unit, and the 3D positioning module is used to detect and acquire human body positioning information and human body type information under the control of the detecting and controlling unit.

Furthermore, with respect to the health multifunctional chair as described above, the detecting and controlling unit further includes a control processing module and a music conditioning module; the music conditioning module includes a sound equipment and an audio collecting module for collecting user voice information, the sound equipment and the audio collecting module are connected to the control processing module; the sound equipment is provided in two, being respectively provided at two sides of the massage backrest and facing positions of two ears; the sound equipment and the audio collecting module are connected to the control processing module.

Furthermore, with respect to the health multifunctional chair as described above, the detecting and controlling unit further includes a touch control module, the chair seat further includes a rotating holder; the touch control module is fixed on an armrest side of the chair seat through the rotating holder, for performing man-machine interaction; the touch control module is electrically connected to the control processing module; the audio collecting module is provided beside the touch control module.

Furthermore, with respect to the health multifunctional chair as described above, the touch control module is further provided with a video camera.

Furthermore, with respect to the health multifunctional chair as described above, the detecting and controlling unit further includes multiple detecting interfaces, for detecting and acquiring user health information; the multiple detecting interfaces include: a 12-lead electrocardio interface, a blood oxygen detecting interface, a blood pressure detecting interface, and a body temperature detecting interface; the health information includes: an electrocardiogram, a blood oxygen value, a blood pressure value, and a body temperature value; the 12-lead electrocardio interface, the blood oxygen detecting interface, the blood pressure detecting interface, and the body temperature detecting interface are all connected to the control processing module.

Furthermore, with respect to the health multifunctional chair as described above, the health analyzing unit includes a data storage module, a data analyzing module, and a health conditioning module:

the data storage module, being used to store the voice information and the health information;

the data analyzing module, being used to analyze the voice information and the health information, and acquire a health analysis result of the user;

the health conditioning module, being used to provide a health solution matched with the health analysis result according to the health analysis result.

The present disclosure further provides a control method for the health multifunctional chair of any one of the preceding, including:

S1: selecting a care device or a health detecting item through the detecting and controlling unit, the care device including: an exercise standing plate and a meridian massage mechanism;

S2: after selecting the care device, controlling the selected care device through the detecting and controlling unit; after selecting the health detecting item, collecting and detecting the health information of the user according to the selected health detecting item;

S3: processing the health information of the user, and acquiring the health analysis result of the user;

S4: providing a corresponding conditioning method and product according to physical condition information of the user.

Furthermore, with respect to the control method as described above, after selecting the care device, if the meridian massage mechanism is selected, the method further includes:

detecting and acquiring human body positioning information and human body type information by a 3D positioning module under the control of the detecting and controlling unit;

performing, by the 3D positioning module, motion detection at one side of the massage backrest contacting a back of the user;

acquiring, by the detecting and controlling unit, a compressed region and an uncompressed region of the massage backrest according to the motion detection, and processing and obtaining bordering position information according to the compressed region and the uncompressed region, taking the bordering position information as the human body positioning information; acquiring the human body type information according to the human body positioning information.

In the above technical solutions, the present disclosure uses the massage backrest with the meridian massage techniques with the characteristics of the traditional Chinese medicine, and can perform combined and ordered meridian massage to the back of the user, thus improving the quality of health maintenance. Meanwhile, the exercise standing plate is further included, enabling the user to do corresponding standing plate exercise through the present equipment, besides, the health management module is further included, therefore, the health analysis result can be acquired according to the detected and acquired health information of the user, and matched with the corresponding health solution; the health solution can provide a corresponding conditioning method or recommend a corresponding health product, thus achieving the object of maintaining or improving the user's health.

BRIEF DESCRIPTION OF DRAWINGS

In order to illustrate the technical solutions of embodiments of the present application or the prior art more clearly, accompanying drawings which need to be used in the description of the embodiments will be briefly described below. Apparently, the accompanying drawings described in the following are merely for some embodiments of the present disclosure, and a person ordinarily skilled in the art still can obtain other accompanying drawings according to these accompanying drawings.

DETAILED DESCRIPTION OF EMBODIMENTS

Figure 1:
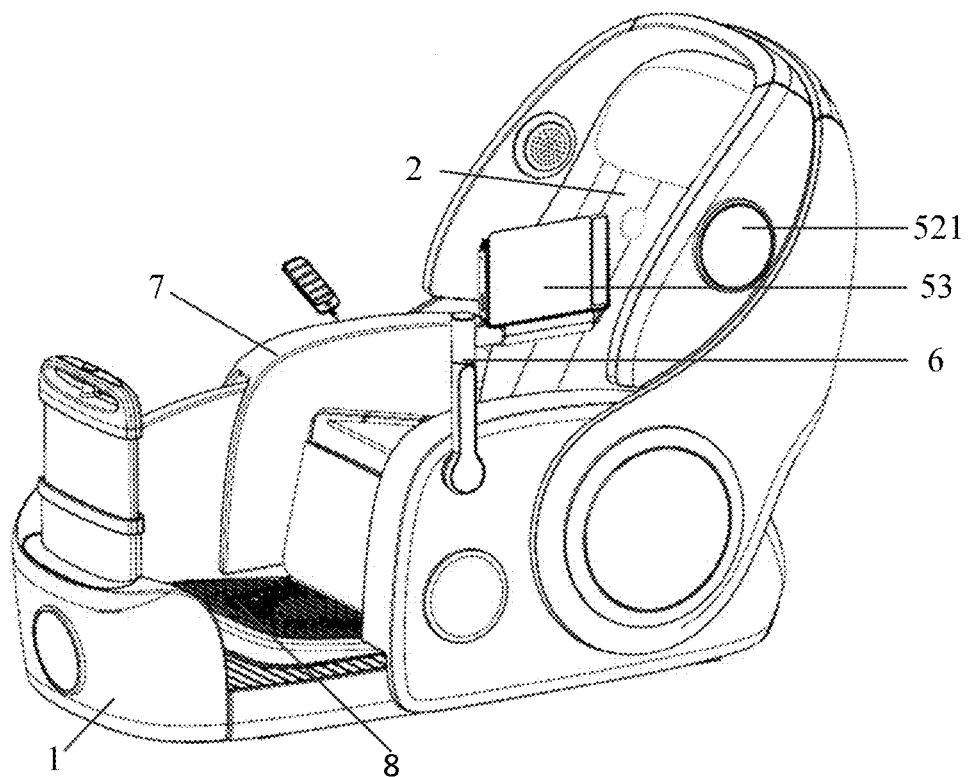
FIG. 1 is a front view of a health multifunctional chair of one of the embodiments.
Figure 2:
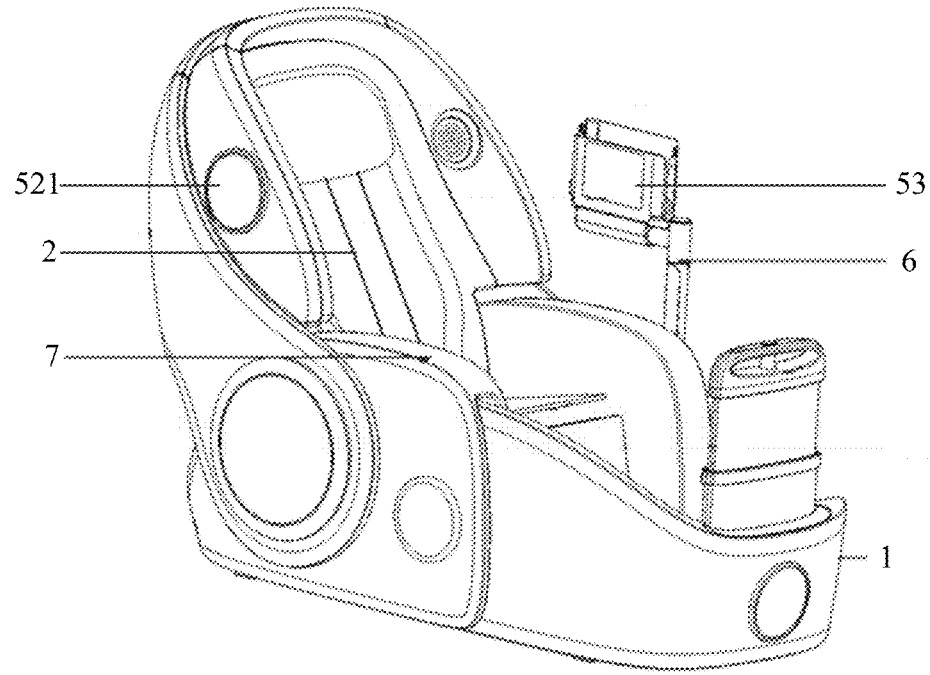
FIG. 2 is a view of the health multifunctional chair of an embodiment of the present disclosure from another angle.
Figure 3:
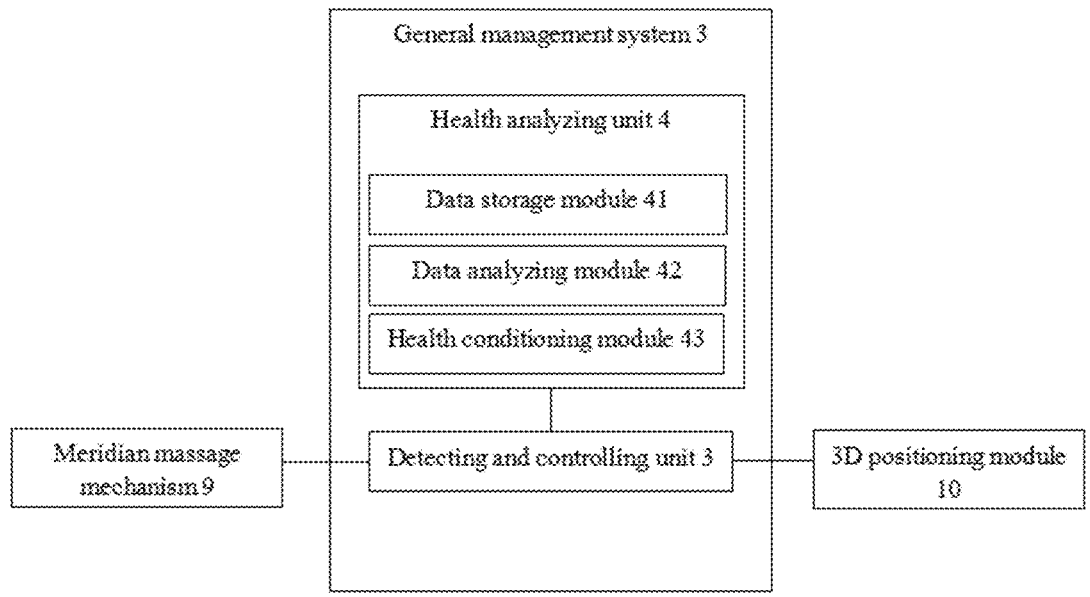
FIG. 3 is a schematic view of connection of function modules of the health multifunctional chair of an embodiment of the present disclosure.
Figure 4:
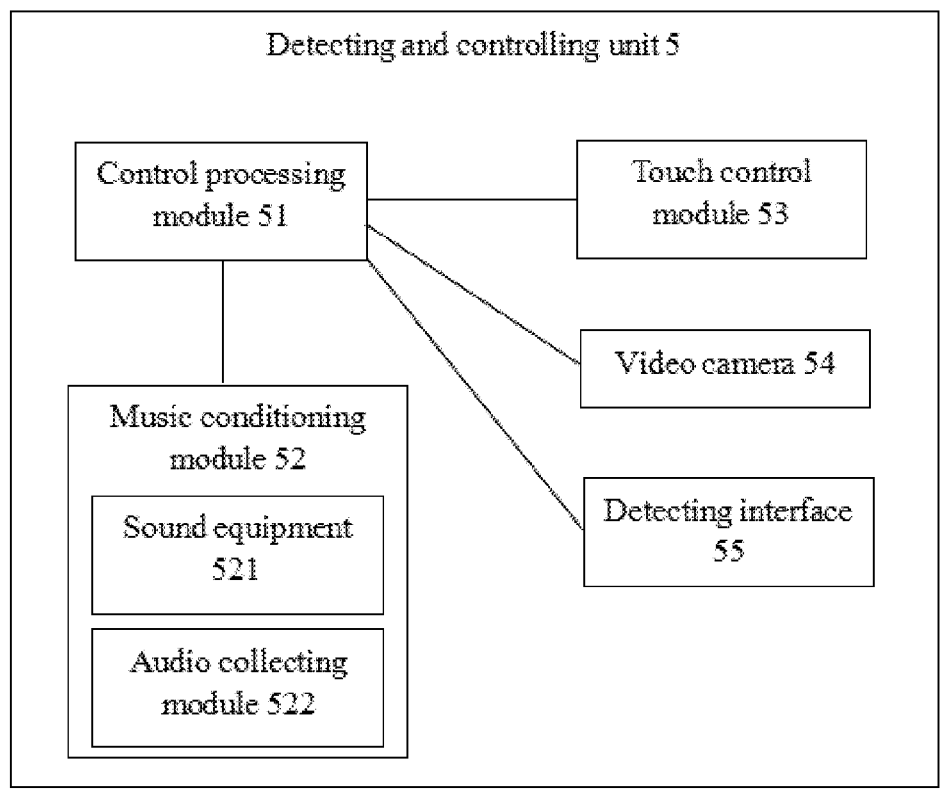
FIG. 4 is a schematic view of connection of modules of a detecting and controlling unit of the health multifunctional chair of an embodiment of the present disclosure.

In order to enable a person skilled in the art to better understand technical solutions of the present disclosure, the present disclosure will be further described in detail below with reference to the accompanying drawings.

As shown in FIG. 1 to FIG. 4, the present disclosure provides a health multifunctional chair, including a chair seat 1, a massage backrest 2, an exercise standing plate 8, and a general management system 3. The general management system 3 includes: a detecting and controlling unit 5 and a health analyzing unit 4; the health analyzing unit 4 is provided locally or on a cloud, and is in communication connection with the detecting and controlling unit 5; the massage backrest is reversibly provided at one side of the chair seat, and the exercise standing plate 8 is provided at the other side of the chair seat; the exercise standing plate 8 can be adjusted in angle with one side edge as a reference and towards a direction of the chair seat 1; the massage backrest 2 is provided with a meridian massage mechanism 9 therein, and the meridian massage mechanism 9 is used to do massage to a back; the health analyzing unit 4 is used to analyze health information of a user collected by the detecting and controlling unit 5, acquire a health analysis result of the user, and provide a health solution; the detecting and controlling unit 5 is further used to manage and control massage of the meridian massage mechanism 9 to corresponding human body positions and angle adjustment of the exercise standing plate 8.

In some embodiments, with respect to the health multifunctional chair, the massage backrest 2 is further provided with a 3D positioning module 10 therein, the 3D positioning module 10 is electrically connected to the detecting and controlling unit 5, and the 3D positioning module 10 is used to detect and acquire human body positioning information and human body type information under the control of the detecting and controlling unit 5. The massage backrest 2 in the present disclosure has the massage function of meridian massage techniques with the characteristics of the traditional Chinese medicine, and can do ordered massage to the back, therefore, in the aspect of health maintenance, through the meridian massage, the systematic all-around health maintenance requirements can be better satisfied, and finally the quality of health maintenance is improved. The detecting and controlling unit 5 is a processing means having data storage, data processing, and communication functions.

In some embodiments, the detecting and controlling unit 5 further includes a control processing module 51 and a music conditioning module 52; the music conditioning module 52 includes a sound equipment 521 and an audio collecting module 522 for collecting user voice information, the sound equipment 521 and the audio collecting module 522 are connected to the control processing module 51; the sound equipment 521 is provided in two, being respectively provided at two sides of the massage backrest 2 and facing positions of two ears; the sound equipment 521 and the audio collecting module 522 are connected to the control processing module 51. Specifically, the audio collecting module 522 is provided on the chair seat 1 for detecting the user voice information. Through embedded software in the general management system 3, detections such as identification of constitution of the traditional Chinese medicine and identification through sound can be performed, and music suitable to this constitution is selected according to the detection result, and played through the sound equipment 521, thus achieving the purpose of music conditioning.

In some embodiments, the detecting and controlling unit 5 further includes a touch control module 53, the chair seat 1 further includes a rotating holder 6, the touch control module 53 is fixed on an armrest side 7 of the chair seat 1 through the rotating holder 6, for performing man-machine interaction; the touch control module 53 is electrically connected to the control processing module 51; the audio collecting module 522 is provided beside the touch control module 53. Therefore, the user can control various action mechanisms through the touch control module 53, for example, the meridian massage mechanism 9 and the music conditioning module 52.

In some embodiments, the detecting and controlling unit 5 further includes a video camera 54, and the video camera 54 is electrically connected to the control processing module 51; the video camera 54 is provided above the touch control module 53, therefore, through the video camera 54 and a corresponding software platform, a video displaying function can be realized, and health consultation can be performed through connection with a background, moreover, the video camera can be connected with a background system through a wired or wireless network, so as to provide to the user guidance and management of health maintenance timely and conveniently.

In some embodiments, the detecting and controlling unit 5 further includes multiple detecting interfaces 55, for detecting and acquiring user health information; the detecting interfaces 55 include: a 12-lead electrocardio interface, a blood oxygen detecting interface, a blood pressure detecting interface, and a body temperature detecting interface; the health information includes: an electrocardiogram, a blood oxygen value, a blood pressure value, and a body temperature value; the 12-lead electrocardio interface, the blood oxygen detecting interface, the blood pressure detecting interface, and the body temperature detecting interface are all connected to the control processing module 51.

In some embodiments, the health analyzing unit 4 includes a data storage module 41, a data analyzing module 42, and a health conditioning module 43;

the data storage module 41 is used to store the voice information and the health information;

the data analyzing module 42 is used to analyze the voice information and the health information, and acquire a health analysis result of the user;

the health conditioning module 43 is used to provide a health solution matched with the health analysis result according to the health analysis result; specifically, the processing analysis can be carried out by a local system with a function of data processing analysis, and the voice information and the physical sign information also can be uploaded through network to a cloud to be analyzed and processed by a server with a data processing function, thus acquiring the health information of the user, wherein the health information can be displayed through the touch control module 53;

the health analyzing unit 4 is used to provide a health management solution matched with the health information according to the health information. The health analyzing unit 4 can be, but not limited to, a local means of a memory and a processor in combination or a means of a memory and a processor in combination on a cloud; the memory can store health management solution data and keywords of the health information; the processor is used to retrieve the health management solution data in the memory according to the keywords of the health information; the health management solution data can be video information (which can be health conditioning exercise video and so on), product link (guiding the user to purchase a product adapted to his/her health management solution), literal contents, and so on.

Figure 5:
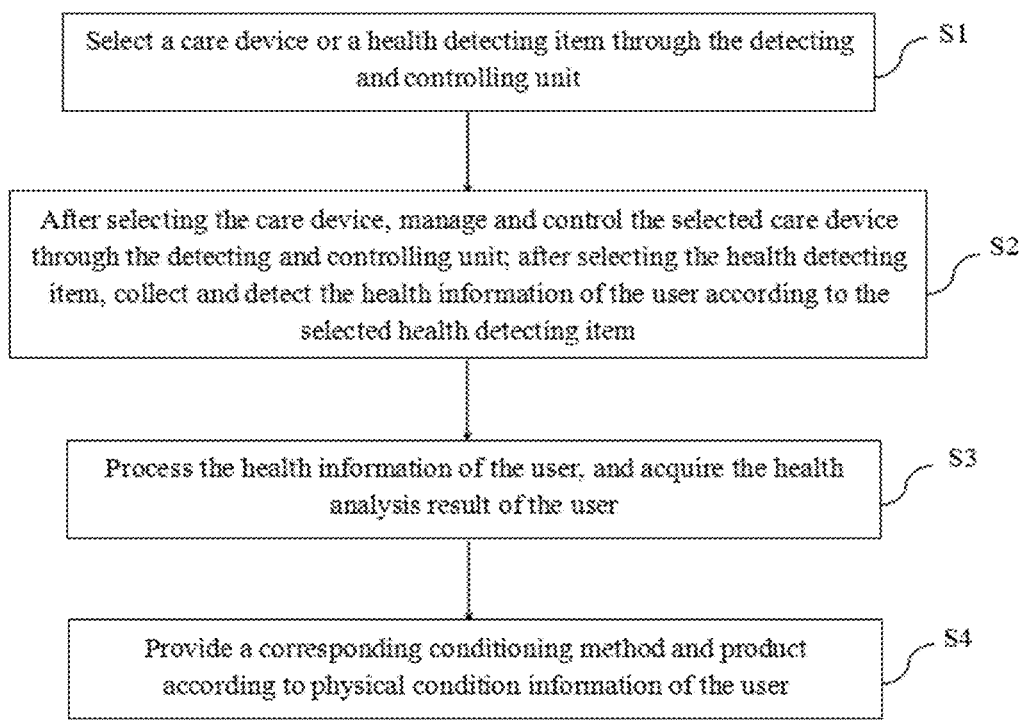
FIG. 5 is a flow chart of a control method for the health multifunctional chair of an embodiment of the present disclosure.

As shown in FIG. 5, the present disclosure further provides a control method for health multifunctional chair, including:

S1: selecting a care device or a health detecting item through the detecting and controlling unit, the care device including: an exercise standing plate 8 and a meridian massage mechanism 9;

S2: after selecting the care device, managing and controlling the selected care device through the detecting and controlling unit 5; after selecting the health detecting item, collecting and detecting the health information of the user according to the selected health detecting item;

S3: processing the health information of the user, and acquiring the health analysis result of the user;

S4: providing a corresponding conditioning method and product according to physical condition information of the user.

In some embodiments, after selecting the care device, if the meridian massage mechanism 9 is selected, the method further includes:

detecting and acquiring human body positioning information and human body type information by a 3D positioning module 10 under the control of the detecting and controlling unit 5;

performing, by the 3D positioning module 10, motion detection at one side of the massage backrest 2 contacting a back of the user;

acquiring, by the detecting and controlling unit 5, a compressed region and an uncompressed region of the massage backrest according to the motion detection, and processing and obtaining bordering position information according to the compressed region and the uncompressed region, taking the bordering position information as the human body positioning information; acquiring the human body type information according to the human body positioning information.

Specifically, the function of health management in the present disclosure further includes:

a multi-user co-management function, being capable of recording usage records of multiple users with the present equipment, meanwhile, recording data respectively of usage of the present equipment each time, health monitoring management, monitoring a certain piece of health information for a long period of time.

The above merely describes some exemplary embodiments of the present invention in an illustrative manner. It goes without saying that a person ordinarily skilled in the art modify the embodiments described through various different manners without departing from the spirit and scope of the present invention. Therefore, the above accompanying drawings and description are essentially illustrative, and should not be construed as limitation to the scope protected by the claims of the present invention.

What is claimed is:

1. A health multifunctional chair, comprising: a chair seat, a massage backrest, an exercise standing plate, and a general management system, wherein the general management system comprises: a detecting and controlling unit and a health analyzing unit; the health analyzing unit is provided locally or on a cloud, and is in communication connection with the detecting and controlling unit; the massage backrest is provided at one side of the chair seat, and the exercise standing plate is provided at another side of the chair seat in a way that said plate can be turned over; the exercise standing plate is adjustable in angle with one side edge as a reference and towards a direction of the chair seat; the massage backrest is provided with a meridian massage mechanism therein, and the meridian massage mechanism is configured to do massage to a back; the health analyzing unit is configured to analyze health information of a user collected by the detecting and controlling unit, acquire a health analysis result of the user, and provide a health solution and the detecting and controlling unit is further configured to manage and control massage of the meridian massage mechanism to corresponding human body positions and angle adjustment of the exercise standing plate,.

wherein the massage backrest is further provided with a 3D positioning module therein, the 3D positioning module is electrically connected to the detecting and controlling unit, and the 3D positioning module is configured to detect and acquire human body positioning information and human body type information under the control of the detecting and controlling unit.

2. The health multifunctional chair of claim 1, wherein the detecting and controlling unit further comprises a control processing module and a music conditioning module; the music conditioning module comprises a sound equipment and an audio collecting module configured to collect user voice information, the sound equipment and the audio collecting module are connected to the control processing module; the sound equipment is provided as two pieces, each piece being respectively provided at a side of the massage backrest and configured to face a head part of the user; and the sound equipment and the audio collecting module are connected to the control processing module.

3. The health multifunctional chair of claim 2, wherein the detecting and controlling unit further comprises a touch control module, the chair seat further comprises a rotating holder, the touch control module is fixed on an armrest side of the chair seat through the rotating holder, and is configured to perform human-machine interaction; the touch control module is electrically connected to the control processing module; and the audio collecting module is provided beside the touch control module.

4. The health multifunctional chair of claim 3, wherein the touch control module is further provided with a video camera.

5. The health multifunctional chair of claim 2, wherein the detecting and controlling unit further comprises multiple detecting interfaces, for detecting and acquiring user health information; the multiple detecting interfaces comprise: a 12-lead electrocardio interface, a blood oxygen detecting interface, a blood pressure detecting interface, and a body temperature detecting interface; the health information comprises: an electrocardiogram, a blood oxygen value, a blood pressure value, and a body temperature value; the 12-lead electrocardio interface, the blood oxygen detecting interface, and the blood pressure detecting interface, and the body temperature detecting interface are all connected to the control processing module.

6. The health multifunctional chair of claim 5, wherein the health analyzing unit comprises a data storage module, a data analyzing module, and a health conditioning module:
the data storage module, configured to store the voice information and the health information;
the data analyzing module, configured to analyze the voice information and the health information, and acquire the health analysis result of the user; and
the health conditioning module, configured to provide a health solution matched with the health analysis result according to the health analysis result.

7. A control method for the health multifunctional chair of claim 1, comprising:
S1: selecting a care device or a health detecting item through the detecting and controlling unit, the care device comprising: the exercise standing plate and the meridian massage mechanism;
S2: after selecting the care device, managing and controlling the selected care device through the detecting and controlling unit; or after selecting the health detecting item, collecting and detecting the health information of the user according to the selected health detecting item;
S3: processing the health information of the user, and acquiring the health analysis result of the user; and
S4: providing a corresponding conditioning method and product according to physical condition information of the user.

8. The control method of claim 7, wherein after selecting the care device, if the meridian massage mechanism is selected, the method further comprises:
detecting and acquiring human body positioning information and human body type information by a 3D positioning module under the control of the detecting and controlling unit;
performing, by the 3D positioning module, motion detection at one side of the massage backrest contacting a back of the user;
acquiring, by the detecting and controlling unit, a compressed region and an uncompressed region of the massage backrest according to the motion detection, and processing and obtaining bordering position information according to the compressed region and the uncompressed region, taking the bordering position information as the human body positioning information; and acquiring the human body type information according to the human body positioning information.

9. A control method for the health multifunctional chair of claim 1, comprising:
S1: selecting a care device or a health detecting item through the detecting and controlling unit, the care device comprising: the exercise standing plate and thea meridian massage mechanism;
S2: after selecting the care device, managing and controlling the selected care device through the detecting and controlling unit; or after selecting the health detecting item, collecting and detecting the health information of the user according to the selected health detecting item;
S3: processing the health information of the user, and acquiring the health analysis result of the user; and
S4: providing a corresponding conditioning method and product according to physical condition information of the user.

10. A control method for the health multifunctional chair of claim 2, comprising:
S1: selecting a care device or a health detecting item through the detecting and controlling unit, the care device comprising: the exercise standing plate and the meridian massage mechanism;
S2: after selecting the care device, managing and controlling the selected care device through the detecting and controlling unit; or after selecting the health detecting item, collecting and detecting the health information of the user according to the selected health detecting item;
S3: processing the health information of the user, and acquiring the health analysis result of the user; and
S4: providing a corresponding conditioning method and product according to physical condition information of the user.

11. A control method for the health multifunctional chair of claim 3, comprising:
S1: selecting a care device or a health detecting item through the detecting and controlling unit, the care device comprising: the exercise standing plate and the meridian massage mechanism;

S2: after selecting the care device, managing and controlling the selected care device through the detecting and controlling unit; or after selecting the health detecting item, collecting and detecting the health information of the user according to the selected health detecting item; and S3: processing the health information of the user, and acquiring the health analysis result of the user;

S4: providing a corresponding conditioning method and product according to physical condition information of the user.

12. A control method for the health multifunctional chair of claim 4, comprising:
S1: selecting a care device or a health detecting item through the detecting and controlling unit, the care device comprising: the exercise standing plate and the meridian massage mechanism;
S2: after selecting the care device, managing and controlling the selected care device through the detecting and controlling unit; or after selecting the health detecting item, collecting and detecting the health information of the user according to the selected health detecting item;
S3: processing the health information of the user, and acquiring the health analysis result of the user; and
S4: providing a corresponding conditioning method and product according to physical condition information of the user.

13. A control method for the health multifunctional chair of claim 5, comprising:
S1: selecting a care device or a health detecting item through the detecting and controlling unit, the care device comprising: the exercise standing plate and the meridian massage mechanism;
S2: after selecting the care device, managing and controlling the selected care device through the detecting and controlling unit; or after selecting the health detecting item, collecting and detecting the health information of the user according to the selected health detecting item;
S3: processing the health information of the user, and acquiring the health analysis result of the user; and
S4: providing a corresponding conditioning method and product according to physical condition information of the user.

14. A control method for the health multifunctional chair of claim 6, comprising:
S1: selecting a care device or a health detecting item through the detecting and controlling unit, the care device comprising: the exercise standing plate and the meridian massage mechanism;
S2: after selecting the care device, managing and controlling the selected care device through the detecting and controlling unit; or after selecting the health detecting item, collecting and detecting the health information of the user according to the selected health detecting item;
S3: processing the health information of the user, and acquiring the health analysis result of the user;
S4: providing a corresponding conditioning method and product according to physical condition information of the user.

15. The control method of claim 9, wherein after selecting the care device, if the meridian massage mechanism is selected, the method further comprises:
detecting and acquiring the human body positioning information and the human body type information by the 3D positioning module under the control of the detecting and controlling unit;
performing, by the 3D positioning module, motion detection at one side of the massage backrest contacting a back of the user;
acquiring, by the detecting and controlling unit, a compressed region and an uncompressed region of the massage backrest according to the motion detection, and processing and obtaining bordering position information according to the compressed region and the uncompressed region, taking the bordering position information as the human body positioning information; and acquiring the human body type information according to the human body positioning information.

16. The control method of claim 10, wherein after selecting the care device, if the meridian massage mechanism is selected, the method further comprises:
detecting and acquiring human body positioning information and human body type information by a 3D positioning module under the control of the detecting and controlling unit;
performing, by the 3D positioning module, motion detection at one side of the massage backrest contacting a back of the user;
acquiring, by the detecting and controlling unit, a compressed region and an uncompressed region of the massage backrest according to the motion detection, and processing and obtaining bordering position information according to the compressed region and the uncompressed region, taking the bordering position information as the human body positioning information; and acquiring the human body type information according to the human body positioning information.

17. The control method of claim 11, wherein after selecting the care device, if the meridian massage mechanism is selected, the method further comprises:
detecting and acquiring human body positioning information and human body type information by a 3D positioning module under the control of the detecting and controlling unit;
performing, by the 3D positioning module, motion detection at one side of the massage backrest contacting a back of the user;
acquiring, by the detecting and controlling unit, a compressed region and an uncompressed region of the massage backrest according to the motion detection, and processing and obtaining bordering position information according to the compressed region and the uncompressed region, taking the bordering position information as the human body positioning information; and acquiring the human body type information according to the human body positioning information.

18. The control method of claim 12, wherein after selecting the care device, if the meridian massage mechanism is selected, the method further comprises:
detecting and acquiring human body positioning information and human body type information by a 3D positioning module under the control of the detecting and controlling unit;
performing, by the 3D positioning module, motion detection at one side of the massage backrest contacting a back of the user;
acquiring, by the detecting and controlling unit, a compressed region and an uncompressed region of the massage backrest according to the motion detection, and processing and obtaining bordering position information according to the compressed region and the uncompressed region, taking the bordering position information as the human body positioning information; and acquiring the human body type information according to the human body positioning information.

19. The control method of claim 13, wherein after selecting the care device, if the meridian massage mechanism is selected, the method further comprises:
   detecting and acquiring human body positioning information and human body type information by a 3D positioning module under the control of the detecting and controlling unit;
   performing, by the 3D positioning module, motion detection at one side of the massage backrest contacting a back of the user;
   and acquiring, by the detecting and controlling unit, a compressed region and an uncompressed region of the massage backrest according to the motion detection, and processing and obtaining bordering position information according to the compressed region and the uncompressed region, taking the bordering position information as the human body positioning information; and acquiring the human body type information according to the human body positioning information.

* * * * *